(12) United States Patent
De Frutos Escrig et al.

(10) Patent No.: US 7,038,089 B2
(45) Date of Patent: May 2, 2006

(54) PROCESS FOR PREPARATION OF HYDROPEROXIDES

(75) Inventors: Pilar De Frutos Escrig, Madrid (ES); Pedro Pablo Toribio Temprado, Madrid (ES); Raul Martos Calvente, Madrid (ES); Jose Miguel Campos Martin, Madrid (ES); Jose Luis Garcia Fierro, Madrid (ES)

(73) Assignee: Respol Quimica, S.A., Madrid (ES)

( * ) Notice: Subject to any disclaimer, the term of this patent is extended or adjusted under 35 U.S.C. 154(b) by 0 days.

(21) Appl. No.: 10/762,792

(22) Filed: Jan. 22, 2004

(65) Prior Publication Data

US 2005/0065381 A1 Mar. 24, 2005

(30) Foreign Application Priority Data

Sep. 24, 2003 (EP) .................................. 03380211

(51) Int. Cl.
*C07C 409/00* (2006.01)

(52) U.S. Cl. .................. 568/564; 568/565; 568/569

(58) Field of Classification Search ................ 568/564, 568/565, 569
See application file for complete search history.

(56) References Cited

U.S. PATENT DOCUMENTS

| | | | |
|---|---|---|---|
| 3,816,540 A | 6/1974 | Barone et al. | |
| 3,949,004 A | 4/1976 | Sorgenti et al. | |
| 4,066,706 A | 1/1978 | Schmidt | |
| 4,158,022 A | 6/1979 | Wu et al. | |
| 4,262,143 A | 4/1981 | Becker | |
| 4,293,720 A | 10/1981 | Iwaki et al. | |
| 4,602,118 A | 7/1986 | Chou et al. | |
| 5,981,420 A | 11/1999 | Nakano et al. | |
| 6,291,718 B1* | 9/2001 | Matsui et al. | 568/569 |
| 6,476,276 B1* | 11/2002 | Matsui et al. | 568/569 |
| 2002/0128149 A1 | 9/2002 | Ishii et al. | |
| 2003/0136603 A1 | 7/2003 | Parghi | |

FOREIGN PATENT DOCUMENTS

| | | |
|---|---|---|
| EP | 0916655 | 5/1999 |
| EP | 0927717 | 7/1999 |
| EP | 1108701 | 6/2001 |
| EP | 1209143 | 5/2002 |
| JP | 9067337 | 3/1997 |
| JP | 9067338 | 3/1997 |
| RU | 2128647 | 4/1999 |
| WO | WO 01/74742 | 10/2001 |
| WO | WO 01/74767 | 10/2001 |

* cited by examiner

*Primary Examiner*—Sikarl A. Witherspoon
(74) *Attorney, Agent, or Firm*—John C. McMahon

(57) ABSTRACT

The invention relates to a process for preparing hydroperoxides from their corresponding hydrocarbons which comprises oxidizing said hydrocarbons, particularly ethylbenzene, with an oxygen containing gas in the presence of a catalyst comprising a cyclic imide compound and a compound selected from the group consisting of an alkali metal compound or mixture thereof.

14 Claims, No Drawings

PROCESS FOR PREPARATION OF HYDROPEROXIDES

FIELD OF THE INVENTION

The invention relates to a process for preparing hydroperoxides from: their corresponding hydrocarbons which comprises oxidizing said hydrocarbons with an oxygen-containing gas in the presence of a catalyst comprising a cyclic imide compound and an alkaline metal compound.

STATE OF THE ART

The preparation of hydroperoxides by reacting appropriate hydrocarbons with molecular oxygen is a well-known reaction which is extensively discussed, for example, in "Organic Peroxides" by E. G. E. Hawkins (D. Van Nostrand Company, Inc. 1961) and in "Organic Peroxides", (3 vols.) edited by Daniel Swern. (Wiley-Interscience, 1970, 1971, and 1972). Homogeneous catalytic oxidation of hydrocarbons with molecular oxygen is very important in chemical industry. A particularly important application of this reaction from a commercial standpoint is the preparation of hydroperoxides which are used for the epoxidation of olefins, especially alkenes such as propylene, to form oxirane compounds, such as propylene oxide. For this purpose the tertiary alkanes, such as isobutane, and the aralkanes, especially ethylbenzene and curriene, as well as the cycloalkanes, such as cyclohexane, are particularly suitable as hydrocarbon feeds. Since the rate of the liquid phase reaction is low in the autoxidation reactions, there have been proposed a wide variety of catalytic systems to enhance the rate of the oxidation, keeping high values of selectivity to the desired product. Process for the preparation of organic hydroperoxides by oxidizing the corresponding hydrocarbon are known from U.S. Pat. Nos. 3,816,540; 3,949,004; 4,066,706; 4,158,022, 4,293,720; 4,602,118; European patents 916655; 927717; 1108701; Japanese patents A-9-67337; A-9-67338; Russian patent 2,128,647 and other documents.

Some authors proposed the use of minute quantity of alkaline metals, as sodium, to increase the yield to organic hydroperoxides in autoxidation of hydrocarbons (U.S. Pat. No. 4,262,143). However, other authors proposed the employ of alkaline-earth compounds (U.S. Pat. No. 4,158,022), particularly barium, showing an increase in the hydroperoxide selectivity when an alkaline-earth salt is added to the reaction mixture.

In the recent years, imide compounds have been found to be active in many: oxidation processes with molecular oxygen due to their properties to start and finish radical chains; for example, in European patent application 1209143 cyblohexanone, cyclohexanol and/or cyclohexyl hydroperoxide are prepared by oxidizing cyclohexane with molecular oxygen using a catalyst comprising a cyclic N-hydroxyimide and a transition metal compound. But, in general, low or none concentration of organic hydroperoxide has been obtained. (U.S. patent application publication 2002/128,149, U.S. patent application publication 2003/0136,603, U.S. Pat. No. 5,981,420, EP 1108701).

On the other hand, others authors propose the use of only imide compounds (WO01/74742, WO01/74767, EP 927717). When high selectivity to organic hydroperoxide was observed, the imide compound concentration was relatively high and hydroperoxide yield was low.

The known processes in which imides are used display the disadvantage of using relatively high concentrations of these compounds in the reaction mixture and moderate temperatures of reaction simultaneously, to get reaction rate and adequate selectivity to make the process suitable for industrial scale. The use of this relatively high concentration of imides in the reaction mixture is undesirable for reasons of cost and because this homogenous catalyst remains in the reaction product as an impurity. This impurity interferes with the ulterior reactions with the hydroperoxide, making necessary expensive and complicated procedures of purification, for example by means of adsorption in inorganic compounds, liquid-liquid extraction, etc. When the imide compound concentration in the reaction mixture is reduced to tolerable levels, the reaction rate is clearly insufficient from the industrial point of view. When low imide compound concentration is used, a rise in the temperature is necessary to increase reaction rate, leading to a decrease of the selectivity to hydroperoxide to unacceptable levels.

Therefore, new processes for hydroperoxides preparation are needed. Specifically desirable are new catalytic systems that allow the selective oxidation of tertiary and secondary alkanes, and alkylaromatics, particularly ethylbenzene, to the corresponding hydroperoxides with high reaction rate. The aim of this invention is to provide a novel, very active catalytic system for the preparation of hydroperoxides, particularly ethylbenzene hydroperoxide. It has now been discovered surprisingly that when the oxidation of ethylbenzene with an oxygen-containing gas is carried out in the presence of a catalytic system comprising a cyclic imide and an alkaline metal compound, simultaneously high reaction rate and high selectivity to hydroperoxide are obtained, superior to those which are obtained when both components from the catalytic system are used independently. Due to the high activity of this catalytic system at relatively low concentrations in the reaction mixture, the cost of the catalyst in comparison with the procedures known in the art is reduced substantially, and the procedures of purification for the elimination of the catalytic rest in the exhaust streams of reaction will not be necessary in the procedure described in this invention.

SUMMARY OF THE INVENTION

The invention relates to a process for preparing hydroperoxides from their corresponding hydrocarbons which comprises oxidizing said hydrocarbons, particularly ethylbenzene, with an oxygen-containing gas in the, presence of a catalyst comprising a cyclic imide compound and an alkali metal compound.

DETAILED DESCRIPTION OF THE INVENTION

According to the present invention, the hydrocarbon is oxidized with molecular oxygen in the presence of a catalyst comprising a cyclic imide compound and an alkaline metal compound.

Examples of the hydrocarbon used in the present invention include tertiary alkanes $C_4$–$C_{20}$ (e.g., iso-butane, iso-pentane, iso-hexane, and the like), $C_7$–$C_{20}$ (alkyl) aromatic hydrocarbons with 1 to 6 aromatic rings or $C_9$–$C_{20}$ (cycloalkyl) aromatic hydrocarbons with 1 to 6 aromatic rings (e.g., xylene, cumene, cymene, ethylbenzene, diisopropyl-benzene, cyclohexylbenzene, tetrahydronaphthalene (tetraline), indane, etc.), and the like.

As a result of the oxidation of the hydrocarbon the main product is a hydroperoxide.

Specifically, the present invention provides a catalyst comprising a cyclic imide compound and a minute amount of an alkali metal compound. In a particular embodiment, the cyclic imide compound has a N-substituted cyclic imide skeleton represented by following formula (1):

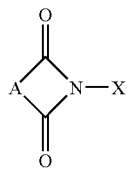

wherein

X is a n oxyl radical or a O-R1 group, wherein R1 is selected from the group consisting of: hydrogen; halogen; hydroxyl; $C_1$–$C_6$ alkyl; $C_6$–$C_{18}$ aryl; $C_3$–$C_{20}$ cycloalkyl; $C_1$–$C_{20}$alkoxy; —CO-R2, wherein R2 is a $C_1$–$C_{20}$ hydrocarbonyl group; —O—CO-R3, wherein R3 is a $C_1$–$C_{20}$ hydrocarbonyl group or a carboxyl group; or —CO—O-R2, wherein R2 is a $C_1$–$C_{20}$ hydrocarbonyl group;

A is —CR4=CR5- or —CR4—CR5- , wherein:

(i) R4 and R5 are independently selected from the group consisting of: hydrogen; halogen; hydroxyl; $C_1$–$C_6$ alkyl; $C_6$–$C_{18}$ aryl; $C_3$–$C_{20}$ cycloalkyl; $C_1$–$C_{20}$ alkoxy; —CO-R2, wherein R2 is a $C_1$–$C_{20}$ hydrocarbonyl group; —O—CO-R3, wherein R3is a $C_1$–$C_{20}$hydrocarbonyl group or a carboxyl group; or —CO—O-R2, wherein R2 is a $C_1$–$C_{20}$ hydrocarbonyl group; or (ii) R4 and R5 taken together with the carbon atoms to which they are joined form a cyclic group, said cyclic group containing 1 to 8 rings, either fused or linked, said rings being aromatic rings or non-aromatic rings, each ring having 3 to 18, members selected from the group consisting of carbon atoms and heteroatoms, such as O, S, N, etc., and being optionally substituted with one or more substituents selected from the group consisting of nitro; phosphine group; phosphonium group; halogen; hydroxyl; $C_1$–$C_6$ alkyl; $C_6$–$C_{18}$ aryl; $C_3$–$C_{20}$ cycloalkyl; or $C_1$–$C_{20}$ alkoxy.

In a particular embodiment, said N-substituted cyclic imide compound of formula (1) is a cyclic N-hydroxyimide. Examples of the cyclic N-hydroxyimide in the present invention include N-hydroxyphthalimide, N-hydroxynaphthalimide, N-hydroxymaleimide, N-hydroxysuccinimide, etc., each one may optionally have at least a substituent. Examples of the substituent include $C_1$–$C_{30}$ alkyl, $C_6$–$C_{18}$ aryl, halogen, nitro, etc. Specific examples of the substituted cyclic N-hydroxyimide include, N-hydroxychloronaphthalimide, N-hydroxynitrophthalimide, N-hydroxychlorophthalimide, etc. The cyclic N-hydroxyimides may be used independently or as a mixture of two or more of them, if necessary.

The amount of the cyclic imide compound used may be from 0.0001 to 1% byweight (wt), preferably from 0.0005 to 0.5% wt based on the reaction mixture.

Examples of the alkali metals contained in the alkaline metal compound include lithium, sodium, potassium and cesium. Among them, sodium and potassium are preferable. Examples of the alkaline metal compound include oxides, organic acid salts, inorganic acid salts, halides, alkoxides, oxoacids and their salts, isopolyacids and their salts, heteropolyacids and their salts, etc., and mixtures thereof. The alkaline metal compound may be used independently or as mixture of two or more of them.

The amount of the alkali metal compound used may be from 0.000005 to 0.01% wt, preferably from 0.00001 to 0.005%. wt, based on the reaction mixture.

In the process of the present invention, the reaction may be carried out in the presence of a solvent. Examples of the solvent include nitriles (e.g. benzonitrile, acetonitrile, etc.), organic acids (e.g. formic acid, acetic acid, etc.), nitro compounds (e.g. nitromethane, nitrobenzene, etc.), chlorohydrocarbons (e.g. chlorobenzene, 1,2-dichloroethane, etc.), and mixture thereof. When the solvent is used, an amount thereof may be at least about 0.01 parts by weight, preferably at least about 0.05 parts by weight and may be a out 4 parts by weight or less, preferably about 1.5 parts by weight or less, per one part by weight of the hydrocarbon.

In the process of the present invention, the oxygen-containing gas is supplied in the reaction medium containing the hydrocarbon, the catalyst, the optional solent, etc., and at the same time, the gas is discharged from the reaction medium. The oxygen-containing gas may be oxygen gas, air, or oxygen gas or air, each of which is diluted with an inert gas or with a combination of inert gasses such as nitrogen gas, helium gas and carbon dioxide. Air is the preferred oxidation gas because of its ready availability but gases richer or poorer in oxygen than air may be used.

The oxygen-containing gas may be supplied in the reaction mixture such that the bubbles of the oxygen-containing gas are dispersed in the mixture containing the hydrocarbon and the catalyst. The oxygen-containing gas may be supplied with a gas-inlet tube or through a nozzle provided in a reactor. The size of the bubbles is appropriately selected. The bubble size may be made small, preferably to 1 mm or less, from the viewpoint of the increase of the reaction rate.

The concentration of the oxygen in the gas discharged from the reaction mixture may be from about 0.1 to about 10% by volume, preferably from about 1 to about 5%. Preferably, the average concentration of the oxygen in the off-gas discharged during the reaction is in the above range. More preferably, the concentration of the oxygen in the gas discharged during the reaction is always substantially in the above range. When, the concentration of the oxygen in the gas discharged is less than about 1% by volume, the selectivity to the desired product may be insufficient. When this concentration exceeds about 5% by volume, the process may suffer from the safety point of view. The concentration of the oxygen can be adjusted by the suitable selection of the kind and amount of the components of the catalytic system, the supply rate and oxygen concentration of the oxygen-containing gas fed, the reaction temperature, the reaction time, the reaction pressure, etc.

In the course of the reaction, one or both of the supply and discharge of the gas may be carried out discontinuously or continuously, if desired. Preferably, the gas is continuously supplied under a constant pressure, and the off-gas is continuously discharged to maintain such pressure.

The reaction temperature at which the hydrocarbon is oxidized may be from 70° C. to about 185° C., preferably from 120° C. to about 175° C., and it is most desirable to operate in the range of about 130° C. to 160° C. At temperatures lower than 110° C., the rate of reaction is undesirably low and temperatures in excess of 175° C. have adverse effect upon selectivity. The reaction could be performed at constant temperature or under programmed temperature conditions.

The reaction pressure may be maintained at from about atmospheric to 10 MPa, although the pressure is desirably maintained at from 0.1 to 1 MPa. The oxidation of hydrocarbons is exothermic and it is, of course, necessary that some heat be removed from the reactor. It is, therefore, most desirable to operate at the adiabatic pressure, that is the pressure at which all of the excess heat produced in the reaction is removed as latent heat of vaporization in boiled-up hydrocarbon. There is then, no requirement for cooling coils or water-jacketed reaction vessels or other types of heat-removal apparatus, nor is there any net heat requirement once, the reaction mixture has been brought to temperature and initiated. The a diabatic pressure depends upon the reaction temperature, the amount of gas fed, the reactant feed temperature, the degree of hydrocarbon conversion, etc., and thus cannot be specifically defined except in relation to these variables. When operating at this pressure, all of the heat of reaction is removed in an overhead vent condenser wherein the boiled up hydrocarbon is condensed and returned to the reaction vessel.

The time required to convert the desired quantity of the hydrocarbon is in the range of from 10 minutes to 20 hours depending upon the temperature maintained in the reactor and the oxygen partial pressure.

The reaction according to the invention can be carried out discontinuously, semi-continuously, or continuously, using a reactor of the adequate kind, for instance a reactor of the stirred tank type, etc. It is possible to use the generally known methods to carry out oxidations with oxygen-containing gas. Thus, the reactants can be added to the reactor in a combined or sequential manner. For instance, the oxygen containing gas and/or the hydrocarbon can be added increasingly to the reactor.

As described above, according to the present invention, the hydroperoxide can be prepared from the corresponding hydrocarbon with a high selectivity thereto by the process which is excellent in the productivity and safety.

In order to illustrate the nature of the invention more fully, and the manner in which it is to be practiced, the following examples are presented

EXAMPLES

Example 1

In a one liter steel autoclave, 520 g of ethylbenzene, 0.52 g of N-hydroxyphthalimide and 175 µl of 0.5% wt NaOH in water solution were charged, and a pressure and a temperature were adjusted at 0.3 MPa and 148° C., respectively, under a nitrogen atmosphere. Through the mixture in the autoclave, an air flow was bubbled for 3 hours while stirring and maintaining the above pressure and temperature. The air flow was controlled to keep an oxygen concentration of 3% by volume at the autoclave gas outlet.

According to the analysis of the reaction mixture, the conversion of ethylbenzene was 21.0%, and the selectivity to acetophenone, 1-phenylethanol and ethylbenzene hydroperoxide was 15.0%, 9.7% and 75.3%, respectively.

Example Comparative 1A

In a one liter steel autoclave, 520 g of ethylbenzene and 175 µl of 0.5% wt NaOH in water solution were charged, and a pressure and a temperature were adjusted at 0.3 MPa and 148° C., respectively, under a nitrogen atmosphere. Through the mixture in the autoclave, an air flow was bubbled for 3 hours while stirring and maintaining the above pressure and temperature. The air flow was controlled to keep an oxygen concentration at the autoclave gas outlet at 3% by volume.

According to the analyses of the reaction mixture, the conversion of ethylbenzene was 17.0%, and the selectivity to acetophenone, 1-phenylethanol and ethylbenzene hydroperoxide was 18.8%, 10.4% and 70.8%, respectively.

Example Comparative 1B

In a one liter steel autoclave, 520 g of ethylbenzene, 0.52, g of N-hydroxyphthalimnide were charged, and a pressure and a temperature were adjusted at 0.3 MPa and 148° C., respectively, under atmosphere. Through the mixture in the autoclave, an air flow was bubbled for 3 hours while stirring and maintaining the above pressure and temperature. The air flow was controlled to keep an oxygen concentration at the autoclave gas outlet at 3% by volume.

According to the analyses of the reaction mixture, the conversion of ethylbenzene was 24.9%, and the selectivity to acetophenone, 1-phenylethanol and ethylbenzene hydroperoxide was 61.9%, 13.5% and 24.6%., respectively.

Example 2

In a one liter steel autoclave, 520 g of ethylbenzene, 0.364 g of N-hydroxysuccinimide and 175 µl of 0.5% wt NaOH in water solution were charged, and a pressure and a temperature were adjusted at 0.3 MPa and 148° C., respectively, under a nitrogen atmosphere. Through the mixture in the autoclave, an air flow was bubbled for 3 hours while stirring and maintaining the above pressure and temperature. The air flow was controlled to keep an oxygen concentration at the autociave gas outlet at 3% by volume.

According to the analyses of the reaction mixture, the conversion of ethylbenzene was 15.9%, and.the selectivity to acetophenone, 1-phenylethanol and ethylbenzene hydroperoxide was 10.5%, 8.2% and 81.3%, respectively.

Example Comparative 2

In a one liter steel autoclave, 520 g of ethylbenzene and 0.364 g of N-hydroxysuccinimide were charged, and a pressure and a temperature were adjusted at 0.3 MPa and 148° C., respectively, under a nitrogen atmosphere. Through the mixture in the autoclave, an air flow was bubbled for 3 hours while stirring and maintaining the above pressure and temperature. The air flow was controlled to keep an oxygen concentration at the autoclave gas outlet at 3% by volume.

According to the analyses of the reaction mixture, the conversion of ethylbenzene was 30.1%, and the selectivity to acetophenone, 1-phenylethanol and ethylbenzene hydroperoxide was 19.2%, 63.9% and 16.9%, respectively.

Example 3

In a one liter steel autoclave, 520 g of ethylbenzene, 0.0742 g of N-hydroxymaleimide and 175 µl of 0.5% wt NaOH in water solution were charged, and a pressure and a temperature were adjusted at 0.3 MPa and 148° C., respectively, under a nitrogen atmosphere. Through the mixture in the autoclave, an air flow was bubbled for 3 hours while stirring and maintaining the above pressure and temperature. The air flow was controlled to keep an oxygen concentration at the autoclave gas outlet at 3% by volume.

According to the analyses of the reaction mixture, the conversion of ethylbenzene was 12.3 %, and the selectivity to acetophenone, 1-phenylethanol and ethylbenzene hydroperoxide was 38.1%, 11.1% and 50.8%, respectively.

Example Comparative 3

In a one liter steel autoclave, 520 g of ethylbenzene and 0.364 g of N-hydroxymaleimide were charged, and a pressure and a temperature were adjusted at 0.3 MPa and 148° C., respectively, under a nitrogen atmosphere Through the Mixture in the autoclave, an air flow Was bubbled for 3 hours while stirring and maintaining the above pressure and temperature. The air flow was controlled to keep an oxygen concentration at the autoclave gas outlet at 3% by volume.

According to the analyses of the reaction mixture, the conversion of ethylbenzene was 14.1%, and the selectivity to acetophenone, 1-phenylethanol and ethylbenzene hydroperoxide was 45.0%, 17.3% and 37.7%, respectively.

Although this invention has been described broadly and also identifies specific preferred embodiments, it will be understood that modifications and variations may be made within the scope of the invention as defined by the following claims.

What is claimed is:

1. A process for preparing a hydroperoxide from a hydrocarbon selected from a group consisting of primary hydrocarbons, secondary hydrocarbons and mixtures thereof corresponding to said hydroperoxide which comprises conducting oxidation of said hydrocarbon at a temperature in the range between 130° and 160° C. with an oxygen-containing gas in a reaction mixture containing said hydrocarbon and a catalyst comprising a cyclic imide compound and an alkali metal compound.

2. The process according to claim 1 wherein the said cyclic imide compound is the compound of formula (1)

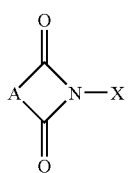

(1)

wherein

X is an oxyl radical or a —O-R1 group, wherein R1 is selected from the group consisting of: hydrogen; halogen; hydroxyl; $C_1$–$C_6$ alkyl; $C_6$–$C_{18}$ aryl; $C_3$–$C_{20}$ cycloalkyl; $C_1$–$C_{20}$ alkoxy; —CO-R2, wherein R2 is a $C_1$–$C_{20}$ hydrocarbonyl group; —O—CO-R3, wherein R3 is a $C_1$–$C_{20}$ hydrocarbonyl group or a carboxyl group; or —CO—O-R2, wherein R2 is a $C_1$–$C_{20}$ hydrocarbonyl group;

A is —CR4=CR5- or —CR4-CR5- , wherein:
  (i) R4 and R5 are independently selected from the group consisting of: hydrogen; halogen; hydroxyl; $C_1$–$C_6$ alkyl; $C_6$–$C_{18}$ aryl; $C_3$–$C_{20}$ cycloalkyl; $C_1$–$C_{20}$ alkoxy; —CO-R2, wherein R2 is a $C_1$–$C_{20}$ hydrocarbonyl group; —O—CO-R3, wherein R3 is a $C_1$–$C_{20}$ hydrocarbonyl group or a carboxyl group; or —CO—O-R2, wherein R2 is a $C_1$–$C_{20}$ hydrocarbonyl group; or
  (ii) R4 and R5 taken together with the carbon atoms to which they are joined form a cyclic group, said cyclic group containing 1 to 8 rings, either fused or linked, said rings being aromatic rings or non-aromatic rings, each ring having 3 to 18 members selected from the group consisting of carbon atoms and heteroatoms, and being optionally substituted with one or more substituents selected from the group consisting of nitro; phosphine group; phosphonium group; halogen; hydroxyl; $C_1$–$C_6$ alkyl; $C_6$–$C_{18}$ aryl; $C_3$–$C_{20}$ cycloalkyl; or $C_1$–$C_{20}$ alkoxy.

3. The process according to claim 1 wherein said cyclic imide of formula (1) is selected from the group consisting of N-hydroxphthalimide, N-hydroxynaphthalimide, N-hydroxymaleimide, N-hydroxysuccinimide, and mixtures thereof.

4. The process according to claim 1, wherein said alkali metal is selected from the group formed by lithium, sodium, potassium and cesium.

5. The process according to claim 1, wherein said alkali metal compound is selected from the group consisting of oxides, organic acid salts, inorganic acid salts, halides, alkoxides, oxoacids and their salts, isopolyacids and their salts, heteropolyacids and their salts, and mixtures thereof.

6. A process for preparing a hydroperoxide from a hydrocarbon corresponding to said hydroperoxide which comprises conducting oxidation of said hydrocarbon at a temperature in the range between 130° and 160° with an oxygen-containing gas in a reaction mixture containing said hydrocarbon and a catalyst comprising a cyclic imide compound and an alkali metal compound wherein the amount of said cyclic imide in the reaction mixture ranges from 0.0001 to 1 percent by weight.

7. The process according to claim 6 wherein the amount of said alkali metal compound in the reaction mixture ranges from 0.00001 to 0.005 percent by weight.

8. A process for preparing a hydroperoxide from a hydrocarbon corresponding to said hydroperoxide which comprises conducting oxidation of said hydrocarbon at a temperature in the range between 130° C. and 160° C. with an oxygen-containing gas in a reaction mixture containing said hydrocarbon and a catalyst comprising a cyclic imide compound and an alkali metal compound wherein the amount of said cyclic imide in the reaction mixture ranges from 0.001 to 0.5 percent by weight.

9. A process for preparing a hydroperoxide from a hydrocarbon corresponding to said hydroperoxide which comprises conducting oxidation of said hydrocarbon at a temperature in the range between 130° and 160° with an oxygen-containing gas in a reaction mixture containing said hydrocarbon and a catalyst comprising a cyclic imide compound and an alkali metal compound wherein the amount of said alkali metal compound in the reaction mixture ranges from 0.000005 to 0.01 percent by weight.

10. The process according to claim 1 wherein the hydrocarbon is an alkane.

11. The process according to claim 10 wherein the hydrocarbon is ethylbenzene.

12. The process according to claim 1 wherein the hydrocarbon is a primary hydrocarbon.

13. The process according to claim 1 wherein the hydrocarbon is a secondary hydrocarbon.

14. A process for preparing a hydroperoxide from a hydrocarbon selected from a group consisting of primary hydrocarbons and mixtures thereof corresponding to said hydroperoxide which comprises conducting oxidation of said hydrocarbon at a temperature in the range between 130° and 160° C. with an oxygen-containing gas in a reaction mixture containing said hydrocarbon and a catalyst comprising a cyclic imide compound and an alkali metal compound.

* * * * *